United States Patent [19]

Allen et al.

[11] 4,022,846

[45] May 10, 1977

[54] PROCESS FOR PRODUCING OLEFINS BY DISPROPORTIONATION

[75] Inventors: John Kenneth Allen, Sale; Brian Michael Palmer, London; Brian Patrick McGrath, Beverley, all of England

[73] Assignee: BP Chemicals International Limited, London, England

[22] Filed: May 21, 1975

[21] Appl. No.: 579,437

Related U.S. Application Data

[62] Division of Ser. No. 264,447, June 20, 1972, Pat. No. 3,903,021.

[30] Foreign Application Priority Data

June 25, 1971 United Kingdom .............. 29872/71

[52] U.S. Cl. ........................ 260/683 D; 260/677 R; 260/680 R
[51] Int. Cl.² ............................................ C07C 3/62

[58] Field of Search ....... 260/683 D, 677 R, 680 R, 260/666 A

[56] References Cited

UNITED STATES PATENTS

| | | | |
|---|---|---|---|
| 3,217,058 | 11/1965 | Hunt | 260/682 |
| 3,448,163 | 6/1969 | Howman et al. | 260/683 |
| 3,535,401 | 10/1970 | Calderon et al. | 260/683 D |
| 3,637,890 | 1/1972 | McGrath et al. | 260/683 |
| 3,668,270 | 6/1972 | Martin et al. | 260/683 |
| 3,721,718 | 3/1973 | Hughes et al. | 260/683 |
| 3,729,525 | 4/1973 | Banks et al. | 260/683 |
| 3,764,635 | 10/1973 | Fattore et al. | 260/683 D |
| 3,792,107 | 2/1974 | Fattore et al. | 260/683 D |
| 3,903,021 | 9/1975 | Allen et al. | 260/683 |

*Primary Examiner*—C. Davis
*Attorney, Agent, or Firm*—Morgan, Finnegan, Pine, Foley & Lee

[57] ABSTRACT

A process for producing olefins by contacting an olefinic feedstock with a rhenium-heptoxide/gamma-alumina disproportionation catalyst.

14 Claims, No Drawings

PROCESS FOR PRODUCING OLEFINS BY DISPROPORTIONATION

This is a division, of application Serial No. 264,447 filed June 20, 1972, now U.S. Pat. No. 3,903,021.

The present invention relates to a catalyst suitable for the disproportionation of olefinic hydrocarbons and to a disproportionation process in the presence of the catalyst.

By disproportionation of olefinically unsaturated hydrocarbon compounds within the context of this invention is to be understood a reaction between two molecules

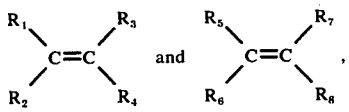

which can be thought to take place by rupture of the double bonds between the radicals

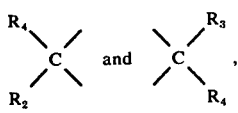

and between the radicals

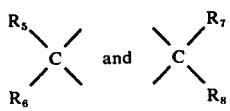

with simultaneous formation of double bonds between the radicals

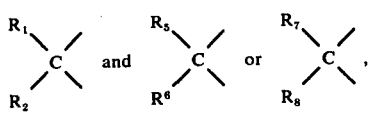

and between the radicals

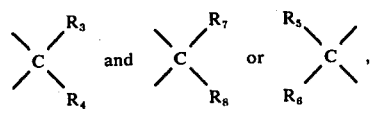

leading to structures

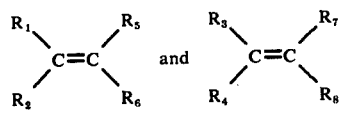

or

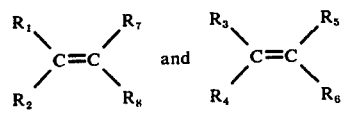

$R_1$, $R_2$, $R_3$, $R_4$, $R_5$, $R_6$, $R_7$, $R_8$, which may be mutually the same or different, may denote hydrogen, alkyl, mono- or polyolefinically unsaturated alkyl, cycloalkyl, mono- or polyolefinically unsaturated cycloalkyl, aryl, alkaryl, mono- or polyolefinically unsaturated alkaryl, alkyl-substituted aryl, aryl substituted with mono- or polyolefinically unsaturated alkyl; one or both of the original olefin molecules may be a cyclic olefin. By way of example the following types of reaction are mentioned, all of which constitute a disproportionation of olefinically unsaturated hydrocarbon compounds (further also to be called olefins) in the purview of this invention:

a. reaction of a molecule of a non-cyclic mono-olefinically unsaturated compound with an identical molecule, giving rise to the formation of mono-olefins with a higher and lower number of carbon atoms then the number of carbon atoms present in the starting olefin, b. reaction of a molecule of an unsaturated compound containing two or more non-conjugated double bonds (e.g. a polymeric compound) with a molecule of the same or another compound containing two or more nonconjugated double bonds.

c. reaction of a non-cyclic mono-olefin with a non-cyclic mono-olefin of other composition, giving rise to the production of two mono-olefins, the sum of the number of carbon atoms of these olefins being equal to the sum of the number of carbon atoms in the original olefins, d. reaction of a non-cyclic mono-olefinically unsaturated compound with a polyolefinically unsaturated compound, e. reaction of a non-cyclic mono-olefin with a cyclic olefin. In this reaction one compound is formed containing a number of carbon atoms which is equal to the sum of the number of carbon atoms present in the cyclic and the non-cyclic olefin, f. reaction of a cyclic olefin with another cyclic olefin of the same or different structure, g. reaction of a cyclic olefin with a poly-unsaturated olefinic compound. In this reaction one compound is formed containing the sum of carbon atoms and double bonds which were present in the reactants. British Patent Specification No. 1,054,864 discloses a process for the disproportionation of acyclic olefins by contacting the olefin with a rhenium heptoxide supported an alumina catalyst.

We have now discovered that gamma-alumina derived from an alumina hydrate prepared by the hydrolysis of aluminum alkoxides formed by oxidation of the products obtained when a low molecular weight aluminium alkyl is reacted with an olefin is a particularly suitable type of alumina for use as a catalyst support because of its reduced tendency to polymerise readily polymerisable olefins and its ability to produce catalysts stable to multi-regenerations.

Thus according to the present invention there is provided a catalyst suitable for the disproportionation of olefinic hydrocarbons which catalyst comprises rhenium heptoxide supported on gamma-alumina obtained by calcination of an alumina hydrate, which alumina hydrate is prepared by a process which comprises the following steps a. reacting an aluminum alkyl of low molecular weight with an alpha mono-olefin to form higher molecular weight aluminum alkyl, b. oxidising the higher molecular weight aluminum alkyls to form the corresponding aluminum alkoxides, c. hydrolysing the aluminum alkoxides to form the alumina hydrate and the corresponding fatty-alcohols, d. recovering the alumina hydrate.

The calcination of the alumina hydrate is suitably effected by heating at a temperature in the range 350° to 600° C in air, nitrogen, etc.

The catalyst preferably contains 0.1 to 40, most preferably 1 to 20 parts by weight rhenium heptoxide per 100 parts gamma-alumina obtained by calcination of the alumina hydrate.

The preferred rhenium heptoxide catalyst may be conveniently prepared by mixing a solution of ammonium perrhenate with the alumina hydrate, drying and heating, preferably in air, to decompose the perrhenate to the heptoxide and to dehydrate the alumina/hydrate to gamma-alumina, or by impregnating the calcined alumina with ammonium perrhenate. A final high temperature activation in nitrogen, carbon dioxide, helium, or other inert gas, or preferably in a stream of air or oxygen followed by a nitrogen treatment, is desirable to generate maximum catalytic activity. Suitably the catalyst is treated in air at a temperature in the range 300° to 900° C for 1 minute to 100 hours and then cooled in a dry, inert gas such as nitrogen.

The aluminium alkyl of low molecular weight preferably contains from 1 to about 6 carbon atoms in the alkyl group. Suitable aluminium alkyls include n-alkyls such as aluminium triethyl, aluminium tripropyl, aluminium tributyl, aluminium trihexyl etc. and aluminium isobutyl, aluminium isopentyls etc. Also included within the scope of the low molecular weight aluminium alkyls are the hydrides formed during the process. These can be either mono- or di-hydrides, for example, in addition to aluminium triisobutyl there can be used in the process aluminium isobutyl dihydride. The aluminium alkyls are perhaps best defined by the formula:

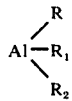

wherein R and $R_1$ are hydrogen or alkyl groups and $R_2$ is alkyl. The preferred aluminium alkyl of low molecular weight is aluminium triethyl.

The alpha mono-olefin reacted with the low molecular weight aluminium alkyl is suitably ethylene, propylene, 1-butene, 1-pentene, 1-hexene etc. but is preferably ethylene.

The reaction can be illustrated by the following equation:

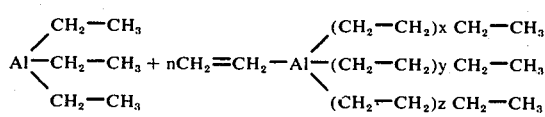

wherein X, Y and Z represent integers in the range 0 to about 28 and $X + Y + Z = n$. The reaction may be carried out by passing the 1-olefin through the low molecular weight aluminium alkyl at a temperature in the range 65° to 155° C, preferably 90° to 120° C and a pressure in the range 200 to 5000 psig, preferably 1000 to 3,500 psig.

The product of the above reaction may be converted partially or entirely to the corresponding aluminium alkoxides by reaction with oxygen in the form of air suitably at a temperature in the range 20° to 100° C and a pressure in the range 10 to 60 psig. By appropriately controlling the quantity of air and the reaction conditions, including the time of reaction, any of the alkyl groups of the aluminum alkyls can be converted to alkoxides. In order to achieve complete oxidation or substantially complete oxidation of the aluminum alkyls the method of U.S. Pat. No. 3,037,954 may be employed. This method involves reacting high molecular weight aluminum alkyls or partially oxidised aluminium alkyls at an elevated temperature with a lower molecular weight aluminium alkyl and thereafter further oxidising the high molecular weight aluminium n-alkyls.

The aluminium alkoxides which are formed in the oxidation step are hydrolysed by contacting them with a conventional hydrolysing agent. Such hydrolysing agents include mineral acids, water, steam and bases. Suitable hydrolying agents include sulphuric acid, sodium hydroxide and potassium hydroxide, to produce aluminium sulphate, sodium aluminate and potassium aluminate repeatedly. A suitable method of hydrolysing the aluminum alkoxides is described in British Patent Specification No. 967,053. The preferred method is described in U.S. Pat. No. 3,394,990 wherein the hydrolysis is accomplished by an n-butanol/water mixture in order to produce directly the alumina hydrate.

If water is used as the hydrolysing medium it is usually necessary to extract the fatty alcohols adsorbed on the alumina hydrate present in the aqueous suspension. A process for effecting this is described in British Patent Specification No. 1,064,317 in which the fatty alcohols are extracted from the alumina hydrate by bringing the alumina hydrate suspension into intimate contact with a substantially water-immiscible alcohol as solvent, separating the solvent phase containing fatty alcohols from the aqueous phase containing the alumina hydrate, and removing the solvent from the solvent phase.

The alumina hydrate may be removed from the system by any suitable means, preferably by filtration. The filter cake may be washed with water or any suitable reagent and dried, usually at elevated temperature and optionally under vacuum.

A suitable alumina hydrate prepared according to the invention may be obtained commercially as a co-product in the Ziegler process for the polymerisation of ethylene for producing long chain - alcohols ("alfols").

According to another aspect of the present invention there is provided a process for the production of olefins which process comprises contacting an olefinic hydrocarbon feedstock with a disproportionation catalyst as hereinbefore described.

Olefinic hydrocarbons suitable as feedstock include acyclic olefins having from 2 to 30 carbon atoms. The acyclic olefins may be straight — or branched — chain olefins in which the double bond may be in any position in the molecule. Examples of olefins suitable as feedstock include ethylene, propylene, butene-1, butane-2, pentene-1, petene-2, 3-methyl butene-1, 4-methyl pentene-2, hexene-1 hexene-2, hexene-3 etc.

The process is particularly useful for olefinic feedstocks containing olefins which are generally regarded as easily polymerisable.

Suitable easily polymerisable olefins include tertiary olefins having the grouping:

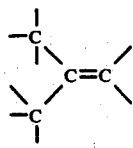

and secondary olefins containing the grouping Ar-CH=C>, wherein Ar represents an aromatic radical.

The particularly easily polymerisable olefin is preferably isobutene.

A very suitable feedstock for the process comprises butene-2 and isobutene since the reaction products, propylene and 2-methyl-butene-2 are highly desirable olefins.

The conditions under which the olefins react may vary with the composition of the feed and the desired products. Reaction temperatures may range from −20° to +500° C, temperatures in the range 20° to 100° C being preferred.

Reaction pressures may be in the range 0 to 2000 psig.

In a continuous process, reaction times may vary between 0.01 second and 120 minutes, preferably between 0.1 second and 10 minutes.

In a batch process, suitable olefin/catalyst weight ratios are in the range 1000:1 to 1:1.

If desired, the process may be carried out in the presence of an inert diluent, for example a paraffinic or cycloparaffinic hydrocarbon.

The catalyst may be regenerated by treatment with oxygen as described in British Patent Specification No. 1,144,085. It is an advantage of catalysts according to the present invention that they retain full selectivity even after many regeneration treatments at temperatures up to 600° C.

The invention is illustrated by the following example:

EXAMPLE

A commercially available high purity alumina hydrate prepared as described in the embodiment of this patent application was used.

The crystallite structure of the starting material was of the boehmite type of typical analysis:

| | |
|---|---|
| $Al_2O_3$ | 75 % |
| C | 0.3 |
| $SiO_2$ | 0.008 |
| $Fe_2O_3$ | 0.005 |
| $Fa_2O_3$ | 0.004 |
| $TiO_2$ | 0.09 |
| Surface Area (BBT) | 190 m$^2$g |

The boehmite was fabricated into a 1/16 inch extrudate and calcined at 550° C to dehydrate the alumina to the gamma-form.

80 g of $NH_4ReO_4$ was dissolved in the minimum quantity of water to totally wet the alumina extrudates and impregnated into 600 g of the extrudates. The material was heated with stirring over a steam bath until nearly dry. The catalyst was dried 4h under vacuum at 100° C.

A commercially available butene stream (selectively hydrogenated and purified as described in our British Patent Specification GB 1,170,498 was passed over this catalyst in a continuous reactor system for 1890 HOS during which time it was regenerated successfully 10 times by oxidative burn off in air at 580° C. The decrease in catalyst activity over this period was negligible.

Typical results for a catalyst cycle are as follows:

| | | | |
|---|---|---|---|
| Reactor Feed | $C_3$'s | | 1.3% wt |
| | i-$C_4^+$ | | 7.0 |
| | n-$C_4^+$ | | 26.4 |
| | i-$C_4^-$ | | 28.0 |
| | n-$C_4^{-1}$ | | 0.2 |
| | n-$C_4^{-2}$(c + t) | | 37.1 |
| | | Total | 100.0 |
| Reaction Conditions | | | |
| | LHSV v/v/h | | 7.0 |
| | Pressure Bar(ga) | | 20 |
| | Temperature ° C | | Programmed 20→80 |
| | Hours on Stream h | | 192 |
| Butene Conversion | | | |
| | To $C_3^-$ | | 12.0% |
| | To $C_5^-$ | | 17.6 |
| | To > $C_5^-$ | | 1.3 |
| | | Total | 30.9 |
| Analyses | | | |
| $C_3^-$Stream | $C_{2+}$'s | | 1.0% |
| | $C_3^+$ | | 1.0 |
| | $C_3^-$ | | 95.9 |
| | $C_4$'s | | 2.1 |
| | | Total | 100.0 |
| $C_5^-$Stream | | | |
| | 2MB1 | | 2.8% |
| | 2MB2 | | 95.8 |
| | Pentene-2(c + t) | | 1.4 |
| | | Total | 100.0 |

This example demonstrates clearly the advantages of high selectivity in the presence of easily polymerisable isobutene and stability of the catalyst to regeneration when the alumina used is one prepared according to the embodiment of this invention.

We claim:

1. A process for the production of olefins which process consists of contacting an olefinic hydrocarbon feedstock capable of undergoing a disproportionation process with an activated disproportionation catalyst at a temperature of between −20° C and +500° C and a pressure of between 0 and 2,000 psig, said disproportionation catalyst comprising rhenium heptoxide supported on gamma-alumina obtained by calcination of an alumina hydrate, which alumina hydrate is prepared by a process which consists of the following steps:
  a. reacting an aluminum alkyl of low molecular weight with an alpha mono-olefin to form higher molecular weight aluminium alkyl,
  b. oxidizing the higher molecular weight aluminium alkyls to form the corresponding aluminium alkoxides,
  c. hydrolyzing the aluminium alkoxides to form the alumina hydrate and the corresponding fatty-alcohols, and
  d. recovering the alumina hydrate.

2. A process according to claim 1 wherein the olefinic hydrocarbon feedstock contains one or more of ethylene, propylene, butene-1, butene-2, pentene-1, pentene-3, 3-methyl butene-1, 4-methylpentene-2, hexene-1, hexene-2, and hexene-3.

3. A process according to claim 1 wherein the olefinic hydrocarbon feedstock is selected from tertiary olefins having the grouping:-

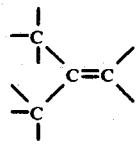

and secondary olefins containing the grouping Ar-CH=C> wherein Ar represents an aromatic radical.

4. A process according to claim 3 wherein the tertiary olefin is isobutene.

5. A process according to claim 1 wherein the olefinic hydrocarbon feedstock consists of butene-2 and isobutene.

6. A process according to claim 1 wherein the reaction time in a continuous process varies between 0.1 second and 10 minutes.

7. A process according to claim 1 wherein the olefin/catalyst weight ratio in a batch process is in the range 1,000:1 to 1:1.

8. A process according to claim 1 wherein the temperature at which the feedstock is contacted with the catalyst is in the range +20° C to +100° C.

9. A process according to claim 1 wherein said activated disproportionation catalyst is activated prior to contacting by treating said catalyst in air at a temperature in the range 300° C to 900° C for one minute to 100 hours, and then cooling it in a dry inert gas.

10. A process according to claim 1 wherein the calcination of the alumina hydrate is effected by heating at a temperature in the range 350° C to 600° C in an inert gas, selected from air and nitrogen.

11. A process according to claim 1 wherein said disproportionation catalyst contains 0.1 to 40 parts by weight rhenium heptoxide per 100 parts gamma-alumina.

12. A process according to claim 1 wherein said aluminium alkyl of low molecular weight is defined by the formula

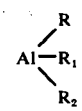

where R and $R_1$ are selected from hydrogen and alkyl groups and $R_2$ is alkyl; and wherein said alpha-mono-olefin is selected from ethylene, propylene, 1-butene, 1-pentene, and 1-hexene.

13. A process according to claim 1 wherein, in the preparation of the alumina hydrate, the product of reaction step (a) is reacted with oxygen in the form of air, at a temperature in the range 20° C to 100° C, and a pressure in the range 10 to 60 psig.

14. A process according to claim 1 wherein, in the preparation of the alumina hydrate, the aluminum alkoxides formed in step (b) are hydrolyzed with a hydrolyzing agent selected from sulphuric acid, sodium hydroxide, potassium hydroxide, and an n-butanol/water mixture.

* * * * *

UNITED STATES PATENT AND TRADEMARK OFFICE
CERTIFICATE OF CORRECTION

PATENT NO. : 4,022,846
DATED : May 10, 1977
INVENTOR(S) : John Kenneth Allen et al.

It is certified that error appears in the above-identified patent and that said Letters Patent are hereby corrected as shown below:

Column 1, lines 21-26, the radical "$R_4$" on the upper left-hand side of the formula should read --$R_1$--;
Column 2, line 11, "then" should read -- than --;
line 43, "an" should read --on--;
Column 4, line 17, "hydrolying" should read --hydrolysing--; line 60, "butane-2" should read --butene-2--;
line 61, "petene-2" should read --pentene-2--;
Column 5, line 10, "CH=C>" should read --CH=C<--;
Column 6, line 7, "$Fa_2O_3$" should read --$Na_2O_3$--;
line 9, "(BBT)" should read --(BET)--;
Column 7, line 14, "of" should read --from--;
line 30, "CH=C>" should read --CH=C<--.

Signed and Sealed this

Eighteenth Day of October 1977

[SEAL]

Attest:

RUTH C. MASON
Attesting Officer

LUTRELLE F. PARKER
Acting Commissioner of Patents and Trademarks